United States Patent
Viegas et al.

(10) Patent No.: US 10,451,549 B2
(45) Date of Patent: Oct. 22, 2019

(54) OPTICAL FIBRE FOR USE IN A SYSTEM FOR DETECTION OF ONE OR MORE COMPOUNDS IN A FLUID

(71) Applicant: INL-International Iberian Nanotechnology Laboratory, Braga (PT)

(72) Inventors: Diana Viegas, Braga (PT); Raquel Queirós, Braga (PT); Jana Nieder, Braga (PT); Maria Teresa Férnandez, Braga (PT); Begoña Espiña, Braga (PT); Paolo Freitas, Braga (PT); Lars Montelius, Braga (PT)

(73) Assignee: INL-INTERNATIONAL IBERIAN NANOTECHNOLOGY LABORATORY, Braga (PT)

( * ) Notice: Subject to any disclaimer, the term of this patent is extended or adjusted under 35 U.S.C. 154(b) by 0 days.

(21) Appl. No.: 15/574,732

(22) PCT Filed: May 16, 2016

(86) PCT No.: PCT/EP2016/060938
§ 371 (c)(1),
(2) Date: Nov. 16, 2017

(87) PCT Pub. No.: WO2016/184825
PCT Pub. Date: Nov. 24, 2016

(65) Prior Publication Data
US 2018/0143133 A1 May 24, 2018

(30) Foreign Application Priority Data

May 18, 2015 (EP) .................... 15167959

(51) Int. Cl.
*G01N 21/552* (2014.01)
*G01N 21/65* (2006.01)
*G01N 21/77* (2006.01)

(52) U.S. Cl.
CPC ......... *G01N 21/554* (2013.01); *G01N 21/553* (2013.01); *G01N 21/658* (2013.01);
(Continued)

(58) Field of Classification Search
CPC .. G01N 21/553; G01N 21/554; G01N 21/658; G01N 21/7703; G01N 2021/7716; G01N 2201/088; G01N 2201/0886
See application file for complete search history.

(56) References Cited

U.S. PATENT DOCUMENTS 6,514,277 B1 * 2/2003 Lilge .................... A61N 5/0601
422/82.08
7,236,812 B1 * 6/2007 Ballerstadt ........... A61B 5/0066
422/82.05
(Continued)

FOREIGN PATENT DOCUMENTS

WO     WO 03/005890 A2    1/2003
WO     WO-2012086198 A1 *   6/2012 ........... G01N 21/658

OTHER PUBLICATIONS

Extended European Search Report dated Nov. 12, 2015 for EP 15167959.4.
(Continued)

*Primary Examiner* — Rhonda S Peace
(74) *Attorney, Agent, or Firm* — Xsensus, LLP

(57) ABSTRACT

The present invention relates to an optical fiber for use in a system for detection of one or more compounds in a fluid. The optical fiber (100, 101, 202) comprising at least two binding portions (102, 104, 118, 210, 211, 212) separated (Continued)

from each other along the longitudinal direction (106) of the optical fiber (100, 101, 202), wherein each of the at least two binding portions (102, 104, 118, 210, 211, 212) comprises a plasmonic structure (120) and/or a SERS structure (121), and a binding material (126) for binding of one or more compounds, wherein at least two binding portions (102, 104, 118, 210, 211, 212) are arranged for binding the same compound or compounds, wherein the optical fiber (100, 101, 202) is arranged for receiving light and transmitting light to each of the at least two binding portions, wherein each of the at least two binding portions (102, 104, 118, 210, 211, 212) is arranged such that light transmitted through that binding portion (102, 104, 118, 210, 211, 212) without bound compound is different compared to light transmitted through that binding portion (102, 104, 118, 210, 211, 212) with bound compound, or light reflected back from that binding portion (102, 104, 118, 210, 211, 212) without bound compound is different compared to light reflected back from that binding portion (102, 104, 118, 210, 211, 212) with bound compound. The present invention further relates to a system (200) for detection of one or more compounds in a fluid (103) and an optical fiber (100, 101, 202) for use in such a system (200) and a method (400) using the system (200).

8 Claims, 5 Drawing Sheets

(52) U.S. Cl.
CPC . *G01N 21/7703* (2013.01); *G01N 2021/7716* (2013.01); *G01N 2201/088* (2013.01); *G01N 2201/0886* (2013.01)

(56) References Cited

U.S. PATENT DOCUMENTS

| | | | | |
|---|---|---|---|---|
| 7,352,468 | B2* | 4/2008 | Tarsa | G01N 21/39 250/227.14 |
| 8,072,606 | B2* | 12/2011 | Chau | G01N 21/554 356/445 |
| 8,305,583 | B2* | 11/2012 | Chau | B82Y 15/00 356/445 |
| 8,355,134 | B2* | 1/2013 | Chau | B82Y 20/00 356/445 |
| 8,411,275 | B1* | 4/2013 | Ohodnicki, Jr. | G01N 21/554 356/437 |
| 8,909,004 | B2* | 12/2014 | Egalon | G01F 23/2927 385/12 |
| 9,464,986 | B2* | 10/2016 | Chau | G01N 21/7703 |
| 9,675,288 | B2* | 6/2017 | Yamakawa | G01N 21/658 |
| 9,964,494 | B1* | 5/2018 | Poole | G01N 21/554 |
| 2004/0186359 | A1* | 9/2004 | Beaudoin | A61B 5/0075 600/310 |
| 2008/0166706 | A1* | 7/2008 | Zhang | G01N 33/54313 435/6.11 |
| 2009/0103851 | A1* | 4/2009 | Tsao | B82Y 20/00 385/12 |
| 2013/0063726 | A1* | 3/2013 | Monro | G01N 21/553 356/445 |
| 2017/0307521 | A1* | 10/2017 | Schade | G01N 21/4133 |
| 2018/0143133 | A1* | 5/2018 | Viegas | G01N 21/553 |

OTHER PUBLICATIONS

International Search Report and Written Opinion dated Jul. 7, 2016 for PCT/EP2016/060938.
Emiliyanov et al., Selective serial multi-antibody biosensing with TOPAS microstructured polymer optical fibers. Sensors (Basel). Mar. 8, 2013;13(3):3242-51. doi: 10.3390/s130303242.
MacLean et al., Detection of hydrocarbon fuel spills using a distributed fibre optic sensor. Sensors Actuators. 2003;109:60-67.

* cited by examiner

OPTICAL FIBRE FOR USE IN A SYSTEM FOR DETECTION OF ONE OR MORE COMPOUNDS IN A FLUID

CROSS REFERENCE TO RELATED APPLICATIONS

The present application is the National Stage under 35 U.S.C. § 371 of PCT International Application No. PCT/EP2016/060938, filed May 16, 2016, which claims the benefit of and priority to European Application No. 15167959.4, filed May 18, 2015, which applications are incorporated herein by reference in their entirety.

FIELD OF INVENTION

The present invention relates to a system for detection of one or more compounds in a fluid and an optical fibre for use in such a system. A method using the system is further provided.

TECHNICAL BACKGROUND

Designing sensors for detecting compounds in fluids such as liquids is of technological importance. Applications range from analysis of the quality or authenticity of food stuff, to environmental studies. The environmental studies may for instance include the detection of cyanobacteria and dinoflagelates in the ocean, lakes and water courses or monitoring of changes in the water quality in those. As an example of the latter, algal blooms, caused by cyanobacteria, are increasing in frequency, duration, geographic extent, and severity in the coastal and freshwater ecosystems. Because these toxins represent a significant hazard to humans, livestock, and wildlife, it is of interest that their concentrations in raw surface waters and finished waters may be routinely quantified.

High-performance liquid chromatography (HPLC) based methods for detecting compounds, such as algal toxins, generally are complex, expensive, and time consuming, in part because of that the analysis cannot efficiently be performed onsite. Simpler screening methods, such as enzyme-linked immunosorbent assay (ELISA), tend to lack specificity and sometimes and are not sufficiently robust.

Thus, there is a need for efficient systems and methods for detection that are field deployable, inexpensive, and which are specific to compounds of interest, for example, toxins or micro-organisms. Moreover there is a need for a high throughput capacity of sampling.

SUMMARY OF INVENTION

One object of the present invention is to solve problems related to prior art.

Another object of the present invention is to provide efficient detection of one or more compounds in a fluid.

According to a first aspect there is provided an optical fibre for use in a system for detection of one or more compounds in a fluid, the optical fibre comprising at least two binding portions separated from each other along the longitudinal direction of the optical fibre, wherein each of the at least two binding portions comprises a plasmonic structure and/or a SERS structure, and a binding material for binding of one or more compounds, wherein at least two binding portions are arranged for binding the same compound or compounds, wherein the optical fibre is arranged for receiving light and transmitting light to each of the at least two binding portions, wherein each of the at least two binding portions is arranged such that light transmitted through that binding portion without bound compound is different compared to light transmitted through that binding portion with bound compound, or light reflected back from that binding portion without bound compound is different compared to light reflected back from that binding portion with bound compound. The optical fibre thereby provides efficient detection of a compound which is bound to the binding portion. The optical fibre is moreover field deployable.

At least two binding portions allows for detection at different locations with a single fibre.

A plasmonic structure and/or a SERS structure, allows for efficient detection of compounds.

A binding material is efficient for binding and thereby detecting a compound with the fibre.

The wording "fluid" should be understood as comprising liquids and gases.

As the at least two binding portions are arranged for binding the same compound or compounds a presence of a compound or compounds along the fibre may be detected.

At least two binding portions may be arranged for binding different compounds. Thus, the presence of a plurality of compounds may be detected.

The binding material may be arranged on the plasmonic structure and/or the SERS structure. Thereby, improved detection efficiency may be realised.

The binding material may comprise functionalising groups or molecular imprints. Thus, selective binding may be realised.

The binding material may comprise a molecularly imprinted polymer. The molecularly imprinted polymer may be targeted for at least one of the at least one compound. Thus, selective binding and detection may be realised.

The optical fibre may comprise a narrow portion, wherein at least one of the at least two binding portions is arranged at the narrow portion.

The distance between the at least two binding portions may be more than 1 m.

The length of the optical fibre may be 10 meter or more.

The fluid may be liquid. The liquid may be, for example, river water, lake water, sea water, process water, waste water, industrial water, liquid food stuffs, or combinations thereof.

According to a second aspect, there is provided a system for detection of one or more compounds in a fluid, the system comprising an optical fibre according to the first aspect, wherein the optical fibre further comprises a light entrance, a light source arranged for transmitting light through the light entrance into the optical fibre and thereby to each of the at least two binding portions, and a detector arranged for detecting light transmitted through the at least two binding portions, or light reflected back from the at least two binding portions.

The light source may be a pulsed light source, preferably a laser.

The light source may be a broad band light source.

The detector may be a time resolving detector.

The detector may comprise a wavelength dispersing element such as a spectrometer.

The entrance and exit may be comprised in a single opening of the optical fibre.

The system may further comprise a transceiver, for transceiving data to, from, or within the system.

According to a third aspect, there is provided a method for analysis of a fluid at a plurality of locations using the system according to the second aspect, wherein at least a portion of the optical fibre is placed in the fluid such that the at least two binding portions are arranged at different locations within the fluid, the method comprising; transmitting light through the optical fibre and thereby to each of the at least two binding portions, detecting light transmitted through the at least two binding portions, or light reflected back from the at least two binding portions, determining if one or more compounds are bound to the least two binding portions respectively.

The method may further comprise comparing data resulting from the determining pertaining to one of the at least two binding portions, with data resulting from the determining pertaining to another one of the at least two binding portions.

Further features of, and advantages with, the present invention will become apparent when studying the appended claims and the following description. The skilled person will realise that different features of the present invention may be combined to create embodiments other than those described in the following, without departing from the scope of the present invention. Features of one aspect may be relevant to anyone of the other aspects, references to these features are hereby made.

BRIEF DESCRIPTION OF DRAWINGS

The above and other aspects of the present invention will now be described in more detail, with reference to appended drawings showing embodiments of the invention. The figures should not be considered limiting the invention to the specific embodiment; instead they are used for explaining and understanding the invention. As illustrated in the figures, the sizes of layers and regions are exaggerated for illustrative purposes and, thus, are provided to illustrate the general structures of embodiments of the present invention. Like reference numerals refer to like elements throughout.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled person.

The optical fibre and the system according to the present invention allows for efficient detection of compounds in a fluid. The plurality of binding portions of the optical fibre makes it possible to analyse the fluid and detecting compounds at different locations of the fluid. The locations may be close or far apart from each other. The fibre may thus be used, for example, for efficient detection of compounds in large volume of fluids, for example, rivers or lakes, or smaller volume of fluids, such as, for example, vessels, reactors or pipes as part of laboratory or process facilities or equipment. As at least two binding portions are arranged for binding the same compound or compounds, the plurality of binding portions further may be used for tracking or detecting changes and movements of compounds in the fluid.

Figure 1:
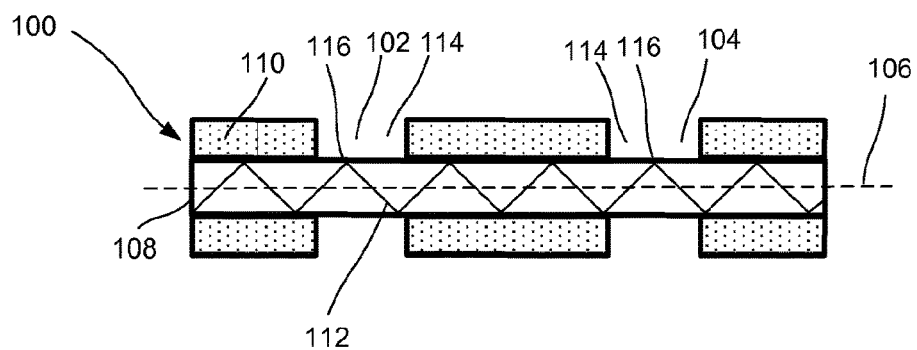
FIG. 1 is a schematic illustration of an optical fibre for use in a system for detection of one or more compounds in a fluid.

FIG. 1 is a schematic illustration of an optical fibre for use in a system for detection of one or more compounds in a fluid. The optical fibre 100 comprises at least two binding portions 102 and 104 separated from each other along the longitudinal direction 106 of the optical fibre 100. Each of the at least two binding portions 102, 104, comprising a plasmonic structure and/or a SERS structure (not illustrated in FIG. 1), and a binding material (not illustrated in FIG. 1), for binding of one or more compounds. The at least two binding portions 102 and 104 are further arranged for binding the same compound or compounds, as will be described below. The optical fibre 100 is arranged for receiving light 112 and transmitting light 112 to each of the at least two binding portions 102 and 104, and each of the at least two binding portions 102 and 104 are arranged such that light 112 transmitted through that binding portion without bound compound is different compared to light 112 transmitted through that binding portion with bound compound, or light 112 reflected back from that binding portion without bound compound is different compared to light reflected back from that binding portion with bound compound.

The optical fibre 100 comprises a core 108 and a cladding 110. The optical fibre 100 is arranged to receive light 112 and to transmit light 112 to each of the at least two binding portions 102, 104. The light 112 may be transmitted in the optical fibre 100 by total internal reflection, TIR. The optical fibre 100 may thereby act as an efficient light guide.

The wording total internal reflection refers to an optical effect that occurs when a ray of light reaches a boundary 116, see FIG. 1, between a first and a second medium at an angle larger than a critical angle, with respect to the normal of the boundary surface. The first medium may be the core 108 and the second medium may be the cladding 110 or the medium, i.e. the fluid, surrounding the optical fibre 100. For TIR to occur it is needed that the refractive index of the first medium is larger than the refractive index of the second material, i.e. in order for the light ray to be essentially fully reflected at the boundary 116 such that essentially no light propagates beyond the boundary and all light is substantially reflected at the boundary.

At the point where the TIR occurs an evanescent wave may, however, be formed, the evanescent wave having an extension beyond the boundary 116, i.e. beyond the first medium. In other words, even though a substantial part of the propagating light 116 is reflected, at the interface of the first and the second medium, back into the first medium, there is some penetration into the second medium at the boundary 116. The evanescent wave in the optically less dense medium, i.e. the second medium may be characterized by its propagation in an x direction, i.e. parallel to the longitudinal direction 106 of the optical fibre 100, and its exponential attenuation in a z direction, i.e. perpendicular to the longitudinal direction 106 of the optical fibre 100. The evanescent wave decays exponentially away from the boundary 116 in the z direction.

To this end, a change in the refractive index of the second medium or a local change of the refractive index in the vicinity of the binding portion 102, 104 may change the efficiency at which the light is propagating within the optical fibre 100. Hence, such a change in the refractive index of the surrounding medium may influence the amount of light and/or the spectral distribution of the light 112 propagating within the optical fibre 100.

At the binding portions 102, 104 the optical fibre 100 may comprise narrow portions 114. The narrow portion 114 may, as illustrated in FIG. 1, extend around the optical fibre 100. It should, however, be noted that in other embodiments the narrow portion may only be formed along a portion of the circumference of the optical fibre.

The narrow portion 114 may be obtained by removing the cladding 110 of a portion of the optical fibre 100 while maintaining the core 108 intact. This changes the optical modes that propagate in the optical fibre 100 such that an optical mode of the core 108 may change in shape such that it is affected to a larger extent by the medium surrounding the narrow portions 114. In other words, the evanescent waves at the narrow portion 114 may be stronger in the outer medium. Such a narrow portion 114 may be achieved by polishing and/or by chemical etching of a portion of the optical fibre 100.

The narrow portion may alternatively comprise a tapered portion, or a double tapered portion. A tapered portion may be achieved by fusing a thinner optical fibre section onto an optical fibre with a larger diameter, or, by a drawing process of an optical fibre such that a single continuous optical fibre with an integral tapered section is formed. The drawing process may comprise heating of a portion of the optical fibre with a heating element or by chemical etching of the optical fibre.

Figure 2A:
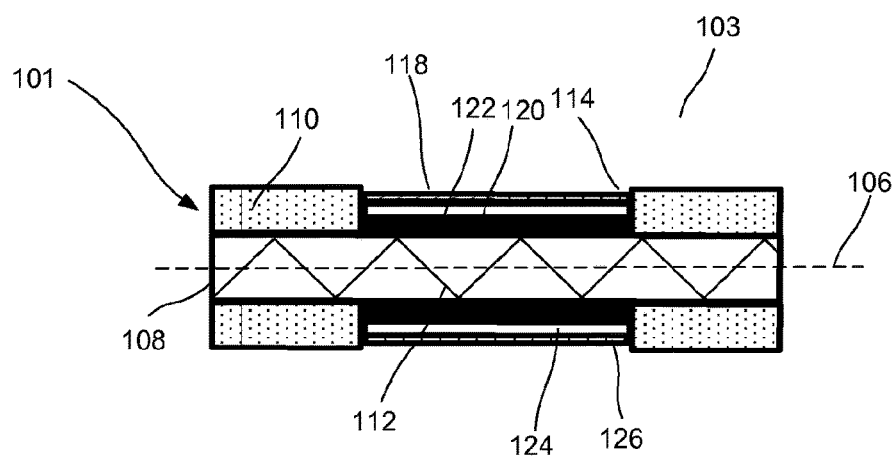
FIG. 2a is a schematic illustration of another optical fibre for use in a system for detection of one or more compounds in a fluid.

FIG. 2a is a schematic illustration of another optical fibre for use in a system for detection of one or more compounds in a fluid. The optical fibre 101 is immersed in the fluid 103. The optical fibre 101 comprises a binding portion 118 arranged at a narrow portion 114 of the optical fibre 101.

The binding portion 118 comprises a plasmonic structure 120. The plasmonic structure 120 is formed by a metal layer 122. The metal layer 122 may be a gold layer. The plasmonic structure 120 may support a surface plasmon resonance, SPR, which may be used as thin-film refractometer, to measure changes in the refractive index occurring at or in the vicinity of the surface of a metal film 122 supporting the surface plasmon. This measurement concept allows for detection of refractive index changes at or in the vicinity of the metal film 122. By measuring changes of the refractive index caused for instance by binding of a compound to the metal film 122, or to a binding material on the metal film, optical sensing of bound compounds, for example biochemical sensing, or sensing of compounds bound to a molecularly imprinted polymer on the metal film 122 may be obtained, as will be discussed further below.

The wording plasmonic structure should be construed as a structure in which plasmons may be excited. Plasmons should here be understood as quanta of plasma oscillations associated with a collective oscillation of charge density. The charges may for instance be provided by electrons.

The wording surface plasmon resonance, SPR, is to be understood as a resonant oscillation of charges at the interface between a negative and positive permittivity material which is excited by for instance light. The resonance condition may be achieved when the frequency of incident photons matches the natural frequency of charges, e.g. electrons, oscillate against the restoring force of for instance a positive nuclei.

To this end, when light comprising a p-polarized component is incident on the plasmonic structure in such a way that the propagation constant and energy of resultant evanescent wave is equal to that of an allowed surface plasmon wave at the interface, a strong absorption of light takes place as a result of transfer of energy and an optical spectrum reflected by the plasmonic structure may demonstrate a sharp dip at a particular wavelength known as the resonance wavelength. In other words, the generated propagating surface plasmon wave attenuates the reflection of light at the plasmonic structure.

The plasmonic structure 120 is arranged in contact with the core 108. The surface plasmon wave may thereby be efficiently excited in the optical fibre 101 as the light travels along the core 108. When a light 112 is reflected in the metal 122 and the coupling conditions are satisfied, a change in the light propagating in the fibre may be induced. The change in the light may be observed as sharp dip or peak in the transmission or reflection of light. This is dip/peak is caused by the energy transferred from the incident photons to surface plasmons, which reduces the energy of the reflected optical signal. The sharp dip can be interrogated by for instance using spectral interrogation. Alternatively, a change in the magnitude of the reflection at the plasmonic structure may be probed by measuring the reflection amplitude of light passing through or being reflected from the plasmonic structure.

The binding portion may further comprise a dielectric layer 124. The dielectric layer 124 may for example comprise $TiO_2$. The dielectric layer 124 may protect the metal layer 122. The skilled person in the art realizes that the dielectric layer may comprise other materials than $TiO_2$. The selection of the dielectric material may be used to for instance tune the wavelength at which the SPR of the metal film 122 occurs. An improved overlap between the light propagating in the optical fibre 101 and the plasmonic structure 120 and the SPR may thereby be achieved. A more efficient excitation of the SPR may thereby be achieved.

The production of the metal layer 122 or the dielectric layer 124 may be achieved through a wide range of techniques from physical to chemical. Some physical vapour deposition techniques may, for example, be used to produce thin layers on optical fibre surfaces.

The binding portion may further comprise an additional metal layer such as chromium arranged between the metal layer and a surface of the optical fibre. The additional layer may improve the adhesion of metal layer to the optical fibre.

The binding portion 118 may further comprise a binding material 126 arranged on the plasmonic structure 120. The binding material 126 is arranged to bind at least one compound.

The binding material 126 may alternatively be arranged on the dielectric layer 124.

As an example, the binding material 126 may comprise molecular imprinted polymer, MIP. In the case of artificial receptors, such as MIPs, a polymeric film may be arranged on the surface of the metal layer 122, or on the surface of a dielectric layer arranged on the metal layer, and thereby within a probe volume of the plasmonic structure 120. A binding of a compound to the MIP may thereby produce a local change in the refractive index in the environment of the plasmonic structure 120. The presence of the analyte in the fluid 103 may thereby be detected when it is bound to the binding material 126.

The optical response of light being transmitted and/or reflected from a binding portion comprising the plasmonic structure to which a compound has been bound may be different compared to light transmitted/reflected back from that binding portion without a bound compound. Hence the optical response may be used to determine the binding of the compound.

The optical fibre may be a single mode fibre or a multi-mode fibre.

The diameter of the core may be in the range of 5 to 100 micrometer.

The diameter of the core may be in the range of 50 to 200 micrometer.

The optical fibre may be arranged to efficiently transmit light within a wavelength range such as the C band, which cover the wavelength range 1.53-1.57 µm.

The optical fibre may alternatively be arranged to efficiently transmit light within the infrared, the visible, and or the near ultra-violet wavelength ranges The narrow portion may be formed by the core and the cladding of the optical fibre being smaller in diameter (not shown). Such a narrow portion may be produced by gently stretching an optical fibre while it is heated e.g. over a flame, such that the core material becomes soft. This procedure makes the fibre thinner over some length of e.g. a few millimeters to centimeters. The procedure may for example be used to form a narrow portion having a diameter on the order of 10 micrometer while the diameter of the optical fibre outside of the narrow portion is on the order of 100 micrometer.

Alternatively, the core of the optical fibre may be removed as a result of the thinning of the optical fibre, i.e. the cladding of the optical fibre acts as the wave guide in the tapered portion.

Figure 2B:
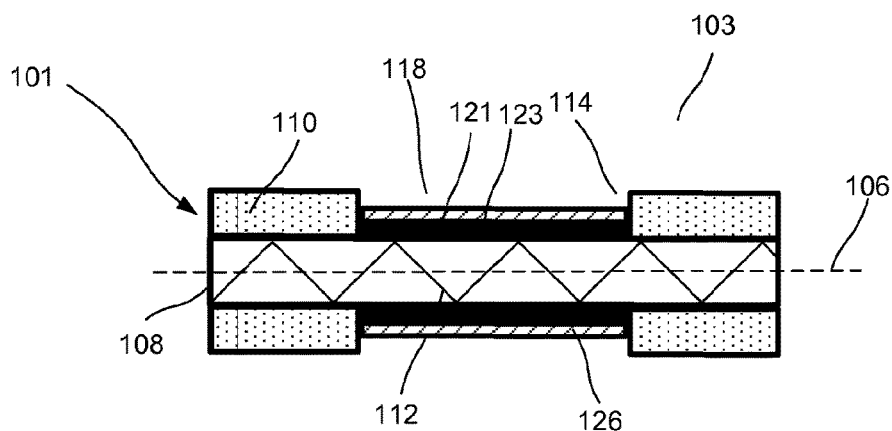
FIG. 2b is a schematic illustration of yet another optical fibre for use in a system for detection of one or more compounds in a fluid.

According to another embodiment, the binding portion 118 may comprises a SERS structure, as illustrated in FIG. 2b. The wording surface-enhanced Raman scattering, SERS, structure should be understood as a structure that enhances Raman scattering by compounds such as molecules adsorbed on the surface of the structure. The enhanced Raman scattering may be used to identify a compound binding to the SERS structure. Hence, the presence of a compound binding to a binding portion may be detected.

In other words, the spectral response of light 112 being transmitted and/or reflected from a binding portion 118 comprising the SERS structure 121 to which a compound has been bound may be different compared to light transmitted/reflected back from that binding portion without a bound compound.

The SERS structure 121 may be a rough metal surface 123 (roughness not illustrated in FIG. 2b) or comprise metal nanostructures (not shown) such that a large surface area may be provided. The SERS structure 121 is further arranged to provide local field enhancement when illuminated by light. In other words, the SERS structure 121 provides concentration of electrical fields at or in the vicinity of the surface of the SERS structure 121. The enhanced electrical fields may increase the excitation efficiency of a compound binding to the surface of the SERS structure 121. The amount of scattered radiation from the adsorbed compound may thereby be enhanced. As a result, an increased Raman scattering signal may be detected for the absorbed compound. Hence, the SERS substrate provides improved detection efficiency of a compound binding to it.

SERS is further advantageous as it requires little to no sample preparation, and may be used in numerous environments. The SERS effect may also be relatively insensitive to the wavelength of excitation employed and may produce a narrowband spectral signature unique to the molecular vibrations of the analyte, i.e. compound bound to the SERS structure. In other words, SERS may efficiently provide a unique molecular fingerprint from which the presence of a compound may be detected with improved sensitivity. The identity of a compound binding to the SERS structure may further be determined from the molecular fingerprint.

A binding material 126 may be arranged on the SERS structure 121. As an example, the binding material 126 may comprise a molecular imprinted polymer, MIP. In the case of artificial receptors, such as MIPs, a polymeric film may be arranged on the surface of the SERS structure 121. Thus, selective binding and detection may be realised and an improved detection efficiency may further be realised.

The SERS structure 121 may comprise a plasmonic structure providing a localised surface plasmon resonance, LSPR (not shown in FIG. 2b). The wording localized surface plasmon resonance, LSPR, is to be understood as an excited state of the charge carriers within the plasmonic structure, which can be excited by photons or, equivalently, by the electromagnetic field of light incident on the plasmonic structure 121. The LSPR condition is a resonance condition associated to the collective oscillation of charge density and to the boundary conditions resulting from the finite size of the plasmonic structure. The plasmonic structure providing LSPR may be achieved by providing nanostructures. The nanostructures may for example be formed by electron beam lithography or hole-mask colloidal lithography.

It should further be understood that the LSPR occurs when the electromagnetic radiation interacts with the plasmonic structure. As a result an enhanced local electromagnetic field is created in the close vicinity of the plasmonic structure. The LSPR is further responsible for the electromagnetic-field enhancement that leads to SERS. The strength of the enhancement and the spatial extent of the enhanced field depend on a number of parameters such as the material, size, shape, and environment of the plasmonic structure. The enhanced electric field is beneficial as it improves the sensitivity of the plasmonic structure.

The metal of the metal layer may for example be selected from a group consisting of Au, Ag, Cu, Al, Mg, Ni, Pd and Pt or alloys comprising at least one metal selected from the group. These materials may provide efficient propagation of surface plasmons.

The plasmonic structure may comprise a semiconductor. It is understood that the semiconductor should comprise a plurality of free charge carriers, i.e. electrons and/or holes such that the semiconductor plasmonic structure may support surface plasmons. This may for instance be achieved by doping the semiconductor.

The SPR may from the above be understood to be sensitive to changes in the material properties of surrounding the plasmonic structure. For example, a change in the dielectric constant affects the wavelength at which the SPR occurs, making SPR based structures efficient sensors. In SPR sensors with spectral interrogation, the resonance wavelength $\lambda_0$ is determined as a function of the refractive index of the environment, $n_0$, of the plasmonic structure. If the refractive index of the environment surrounding the plasmonic structure is altered the resonance wavelength may shift in wavelength.

Figure 3A:
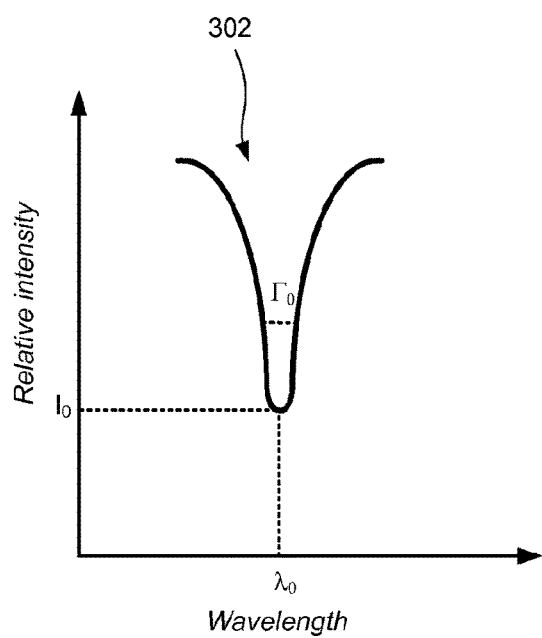
FIGS. 3a and 3b exemplify the detection of a compound in a fluid binding to a binding portion.
Figure 3B:
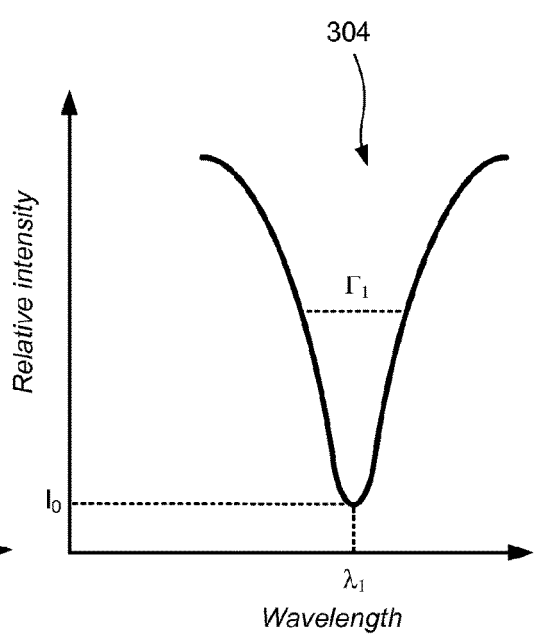

FIGS. 3a and 3b exemplify the detection of a compound in a fluid binding to a binding portion. The binding portion comprises a plasmonic structure providing a SPR. FIG. 3a illustrates optical response from the optical fibre described above in relation to FIG. 2a without the presence of the compound. Light from a light source that is reflected by and/or transmitted through the optical fibre may be acquired by a detector. The light source may for example be a high brightness white LED or a super continuum laser providing efficient broad band illumination.

An extinction spectrum 302 pertaining to the excitation of a SPR of the plasmonic structure 120 is obtained by use of the processing unit and conventional methods to, for instance, normalize light from the light source of electromagnetic radiation.

The extinction spectrum 302 has characteristic features resulting from the choice of plasmonic structure 120 and the materials used in the optical fibre 101. The extinction spectrum 302 may be described by parameters such as the centre wavelength $\lambda_0$, and the peak intensity $I_0$, and the full width at half maximum $\Gamma_0$ of the spectrum. The parameters may be determined by the processing unit by analysing the extinction spectrum 302.

FIG. 3b illustrates the same optical fibre 101 described above but now with the presence of the compound in the fluid 103. As a result of the binding of the compound to the binding material 126 an extinction spectrum 304 is instead obtained, as illustrated in FIG. 3b. In this example the extinction spectrum 304 has a centre wavelength $\lambda_1$, and the peak intensity $I_1$, and the full width at half maximum $\Gamma_1$ which all differ from those of spectrum 302. By detecting at least one of the differences between the two extinction spectra 302 and 304 the presence of the compound in the fluid 103 is detected. A person skilled in the art realizes that other type of optical processes such as absorption may instead be monitored in order to detect the binding of the compound. It should be noted that in other embodiments only one of the disclosed changes to the optical properties of the plasmonic structures may be present which may correspond to a change of at least one of a spectral shift of resonance frequency, an amplitude shift, i.e. a change in magnitude, of optical cross-section, and a change of the full-with of half maximum.

According to some embodiments the plasmonic structure may provide a localised surface plasmon resonance, LSPR. An optical spectrum pertaining to the LSPR of the plasmonic structure may be obtained by illuminating the plasmonic structure with a broad band light source and detecting light reflected and/or scattered by the plasmonic structure. Alternatively monochromatic light may be used to excite the LSPR.

The binding of a compound to the binding portion may change the LSPR of the plasmonic structure. Hence, a detected change in the optical response, i.e. optical spectra and/or a change in the light intensity of light reflected and/or scattered by the plasmonic structure indicates the binding of compound to the binding portion.

A plasmonic structure providing LSPR may be achieved by providing metal nanostructures. The LSPR spectral position depends on the composition, size or shape and the arrangement of the nanostructures, as well as the refractive index of the refractive index of the materials surrounding the nanostructures. Hence, a compound binding to the binding portion may change the refractive index of the surrounding leading to a change of the LSPR. The fabrication of nanostructures is known to the skilled person in the art and may for example be formed by electron beam lithography or hole-mask colloidal lithography.

Figure 4:
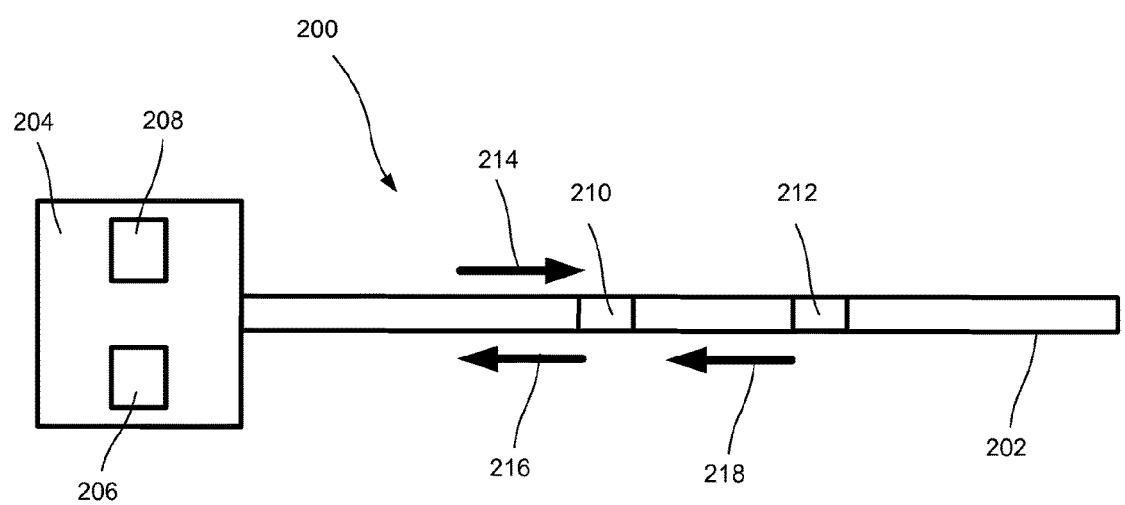
FIG. 4 illustrates a system for detection of one or more compounds in a fluid according to an embodiment.

FIG. 4 illustrates a system 200 for detection of one or more compounds in a fluid according to an embodiment. The system 200 comprises an optical fibre 202, for example the optical fibre 202 according to the embodiment discussed with reference to FIG. 1, 2a or 2b, wherein the optical fibre 202 comprises a light entrance and a light exit. The light entrance and the light exit are inside the housing 204 and not visualised in FIG. 4.

The housing 204 further comprises a light source 206 arranged for transmitting light through the light entrance into the optical fibre 202 and thereby to each of the two binding portions 210, 212, and a detector 208 arranged for detecting light reflected back from the at least two binding portions 210, 212.

The light source 206 may be a laser. The detector 208 may be a light sensitive detector 208. The light sensitive detector 208 may be a time resolving light sensitive detector 208. In this particular example, light reflected back from the two binding portions 210, 212 are considered and discussed.

It should be noted that in this embodiment the system 200 is operated in a reflection mode, i.e. light is sent into the optical fibre 202 via the light entrance and reflected light from within the optical fibre 202 is extracted via the light exit.

The light entrance and the light exit may be the same.

When using the system 200 for detection of compounds in a fluid, at least a part of the optical fibre 202 is positioned in the fluid such that the at least two binding portions 210, 212 are contacted with the fluid. If the fluid, for example, is a liquid, the optical fibre 202 may be submerged in the fluid, but alternatively the optical fibre 202 may be positioned floating on the surface of the liquid, or a combination of submerging and floating may be used. The light source 206 is arranged to transmit light into the optical fibre 202, whereby the light will be transmitted through the optical fibre 202 in the direction indicated by arrow 214, when the light reaches binding portion 210, the light may in part pass through binding portion 210, and may in part be reflected from binding portion 210 and back towards the light source 206 and the detector 208 in a direction indicated by arrow 216. Light passing binding portion 210 will be transmitted to binding portion 212, where light in part may pass through binding portion 212, and in part may be reflected from binding portion 212 and back towards the light source 206 and the detector 208 in a direction indicated by arrow 218.

It is realised that the housing 204 of the system is not necessary for performing the embodiment, and that the illustrated embodiment would function without the housing 204. Further the housing 204 may be provided with, not illustrated, opening means, for example, for providing access to the housing interior or for cables etc.

The system 200 may be set up in SERS-mode, whereby the detector is set up for analysing spectral information in the light reflected back from the binding portions 210, 212, or in SPR-mode whereby the detector 208 is arranged to analyse intensity of light reflected back from the binding portions 210, 212.

The binding portions 210, 212 are arranged such that light reflected back from a binding portion 210, 212 is different when compounds are bound to the binding portions 210, 212 as compared to if no compounds are bound. In SERS-mode bound compounds may provide relevant spectral information, and in SPR-mode bound compounds may result in changes in light intensity and/or spectral distribution of the detected light due to a difference in the refraction index of the binding portion resulting from the bound compounds.

In the SERS mode the light source 206 is preferably a monochromatic laser and the detector 208 may comprise an interference filter such as a notch filter arranged to block the light of the laser. The linewidth of the laser may, for example, be below 1 nm allowing for efficient detection of individual Raman modes. The emission wavelength of the laser may further, for example, be selected from the group of wavelength consisting of 532 nm, 633 nm, 785 nm, 1064 nm, and 1550 nm. The suitable output power of the laser light depends on application and may, for example, range from 10 mW to 1 W. The skilled person in the art realizes that other laser wavelengths and laser powers may be used.

In the SPR mode, the light source 206 may be a monochromatic light source, but may preferably be a broad band light source such as a white light emitting diode or a super continuum laser. Alternatively the light source may be a xenon arc lamp. The broad band light source may thereby efficiently provide light over broader spectral ranges such that the spectral characteristics of the reflected light from a plasmonic structure may be analyzed by the detector 208, as illustrated in FIGS. 3a and 3b. The detector 208 may comprise a wavelength dispersing element from resolving the spectral characteristics of the reflected light.

The wording broad band should here be understood as illumination spanning over a spectral range of different wavelength. The spectral range may for example span over 20-1000 nm, depending on application. Hence, the spectral range may be broad enough to allow for the acquisition of a extinction spectrum as discussed above.

Further, a difference may be registered if more compared to less compounds are bound. In the case with SERS, the difference will be resulting from a difference in the intensity of the light detected.

In the case with SPR the differences will be due to differences in an intensity modulation and/or a spectral shift induced by of the refractive index of the surface to which compounds may be bound or not bound. These differences may be registered by the detector 208. Thus, it is possible to determine, using the system 200, if compounds have been bound to one or more of the binding portions 210, 212, such as, for example, by comparing with analysis data obtained with no bound compounds.

By using a pulsed light source 206 and a time resolving detector 208, it may further be determined which of the binding portions 210, 212 that have bound compounds. The light source 206 and the detector 208 may thereby be seen as parts of a light optical time-domain reflectometer (OTDR) system. An OTDR is to be understood as an optical equivalent of an electronic time domain reflectometer. The OTDR may injects a series of optical pulses into the fibre 202 detect from the same end of the fibre, light that is reflected by a binding portion 210, 212. The light source 206 may, for example, emit light at the wavelength of 1550 nm with a pulse duration of, for example, 3 ns to 20 μs. The time resolution of the detector 208 analysis of light reflected from individual binding portions 210, 212. Information pertaining to which of the biding portions has bound a compound may thereby be obtained. Each binding portion 210, 212 comprises a plasmonic structure and/or a SERS structure (not illustrated), and a binding material (not illustrated) for binding of one or more compounds. The binding material on each of the binding portions 210, 212 has affinity for one or more specific compounds, or one or more group of compounds, respectively. Thus, one binding portion may be arranged to bind one or more specific compounds while another binding group may be arranged for binding of one or more groups of compounds. As one alternative, two or more binding groups, such as all binding groups, may be arranged for identical binding. As another alternative, one binding group may be arranged for binding of one or more specific compounds while another binding group may be arranged for binding of one or more groups of compounds. Binding may refer to reversible binding or irreversible binding of compounds to the binding portion.

Groups of compounds may be selected from, for example, the group consisting of organic compounds, such as aliphatic or aromatic hydrocarbons, alkanes, alkenes, alkynes, alcohols, carboxylic acids, aldehydes, organic sulphides, esters, amine, amide, ketones and compounds that may be present in, for example, algal toxins or combinations thereof. The compounds may be, for example, compounds selected from this group of compounds, or they may be any other suitable compounds.

The one or more compounds may be selected from the group consisting of algal toxins.

It is further realised that the system may be for detection of one or more elements or one or more microorganisms in addition to or instead of compounds.

The binding material may be any suitable material suitable for binding of the compounds or group of compounds of interest. For example, the binding material may be a hydrophobic material, such as a material comprising a hydrophobic polymer or hydrophobic modifiers, for example selected from organic acids or alkanes. Such hydrophobic materials may be suitable for binding of organic compounds or group of compounds, which compounds in the particular fluid of interest has an affinity for binding to the hydrophobic binding material. Alternatively, the binding material may be a hydrophilic binding material, such as, for example, a hydrophilic polymer, or other hydrophilic materials. Such hydrophilic materials may be suitable for binding of hydrophilic compounds or group of compounds, which compounds in a particular fluid of interest has an affinity for binding to the hydrophilic binding material.

For providing ability of specific binding, or specific binding of specific compounds or group of compounds, the binding material may comprise, molecularly imprinted polymers. Molecular imprinted polymers as used herein refers to polymers having sites or cavities, in the form of molecular imprints, with a specific affinity for binding of the specific compounds or group of compounds. The specificity may be related to physical properties such as shape and size of the site or cavity and/or interaction properties. For example, the molecular imprint may have a three dimensional shape corresponding to at least a portion of the shape of the compound to be bound, or to the shape a group being a part of the compound to be bound. Further the molecular imprint may have chemical groups correlated and able to interact with the chemical group of the compound, such as hydrophobic interaction or hydrophilic interaction, for example the ability to create hydrogen bonds. Further, specific binding may be realised with a binding material comprising antibodies.

Figure 5:
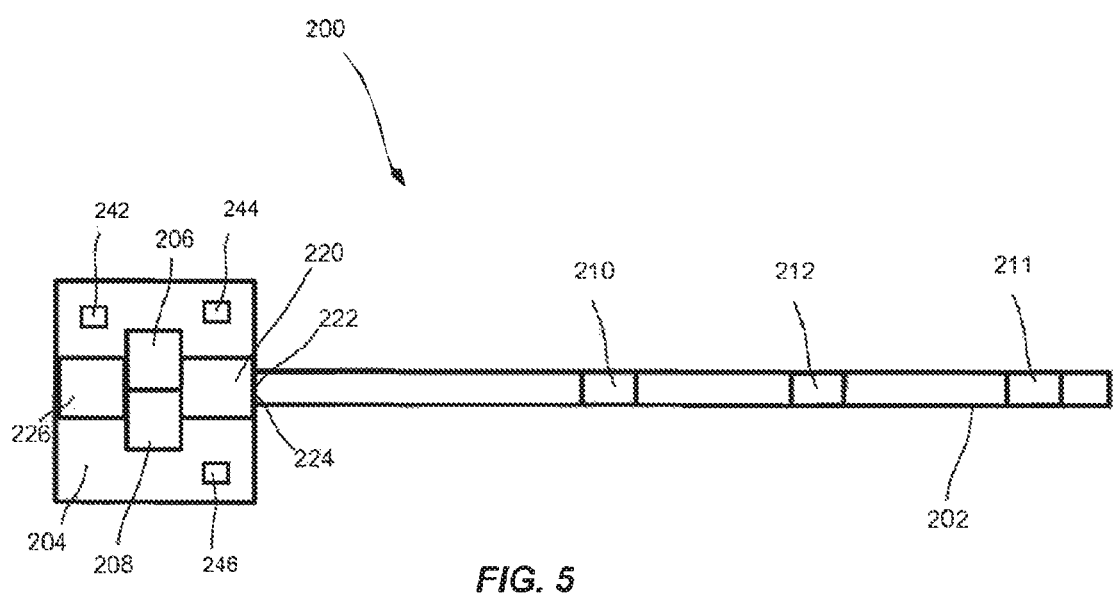
FIG. 5 illustrates a system for detection of algal toxins in a river.

With reference to FIG. 5, a system 200 for detection of algal toxins in a river will now be discussed by means of an example. The system 200 comprises an optical fibre 202 having a length of approximately 1010 meters and a first binding portion 210 positioned approximately 10 meters from a housing 204, a second binding portion 212 positioned approximately 600 meters from the housing, and a third binding portion 211 positioned approximately 1005 meters from the housing adjacent to an end of the optical fibre 202. For improving the clarity of the example only three binding portions 210, 211, 212 are used in the example, although it should be realized that considerably more could be used, such as for example hundreds or thousands of binding sites, or only two binding sites. The housing 204, which is illustrated with its cover off for providing visibility of objects contained in the housing 204. The housing 204 comprises a time resolving detector 208, a light source 206 being a monochromatic light source such as a laser, means 220 for splitting and focusing beams, and arranged for allowing light to be efficiently transferred from the light source 206 into the optical fibre 202 via a light entrance 222, and out from the optical fibre 202 to the detector 208 via a light exit 224. Further, the housing 204 comprises a control device 226 for controlling the detector 208 acid the light source 206 and optional processing or storing of detector data, and optional memory 242, antenna 244, and transceiver 246.

Each of the binding portions 210, 211, 212 comprises a plasmonic structure with an outer layer of polymer being molecularly imprinted against a toxin.

A major part of the optical fibre 202 is positioned in a river, essentially stretched out in its entire length downstream and along the longitudinal direction of the river, and arranged submerged in the river water, while the housing 204 and the first 5 meters of the optical fibre 202 adjacent to the housing 204 are positioned at the river bank.

The system 200 of the discussed example is used for analysing the river water with respect to presence of the toxin. In the example, the binding of the toxin to the molecular imprints is reversible binding, which in this example functions in combination with the flowing water of the river such that essentially no toxin remains bound to the binding portion after a few seconds, if not new toxin is presented in the water surrounding the binding portion.

The detector 208 and the light source 206 together with other devices of the housing 204 is monitoring the optical fibre 202 by transmitting a pulse of light into the optical fibre 202 and detecting light reflected back from each of the three binding portions 210, 211, 212. By using a time resolving detector 208, and pulsed light from a pulsed light source 206, light reflected from each binding portion may be detected separately and thus, it may be determined which of the binding portions that may or may not have bound compounds. For example, detection of compounds according to the embodiment discussed with reference to FIG. 5 may be conducted according to the below.

At time $t_0$, when no compounds have been bound to anyone of the binding portions 210, 211, 212, a light pulse is transmitted into the optical fibre 202. When the light is transmitted to each of the binding portions 210, 211, 212, a fraction of the light will be reflected back towards the light source 206 and the detector 208, as an echo, and due to the positioning of the binding portions at different positions along the optical fibre 202 and the time resolving detector 208, the detector 208 will detect a separate signal for each binding portion 210, 211, 212. The system 200 may thereby be understood as a light optical time-domain reflectometer (OTDR) system. At time $t_1$, when for the sake of the example we assume that toxin has been bound to the first binding portion 210 but to none of the second or third binding portions 212, 211, and as one result changes the refractive index of the surface of the first binding portion 210, the detection signal resulting from the echo from the first binding portion will be different as compared to the corresponding detection signal from the $t_0$ measurement. The detection signal from the second and third binding portions 212, 211 will, resulting from that no compounds have bound to the surface, remain essentially unchanged as compared to the $t_0$ measurements. Later, at time $t_2$ being 5 minutes after $t_1$, a difference in detection signal from the second binding portion 212 is detected, while the detection signal from the remaining binding portions 210, 211 are essentially identical with the corresponding signals at $t_0$. At time $t_3$, 10 minutes after $t_1$, a difference in detection signal from the third binding portion 211 is detected, while the detection signal from the remaining binding portions 210, 212 are essentially identical with the corresponding signals at $t_0$. At time $t_4$, 100 minutes after $t_0$, the detection signal from all three binding portions 210, 211, 212 are essentially identical with the corresponding signals at $t_0$, and the same results are obtained at time $t_5$ one day after $t_0$.

It may be concluded from the example that toxin was released in the river at or upstream the first binding portion, which toxin moved downstream. The day after no toxin was detected at the time of the measurements. It is realised that a system with a longer optical fibre may be used, such as a 10 km long optical fibre with binding portions for example every ten meter. Such a system could be used for example in a lake or in a river to detect the presence of toxins, and further to detect locations where releases are made, and to track the spreading or movement of the toxin. It is further realised that shorter fibres may be used, such as fibres having lengths of 100 m, or below, such as 10 meters or below. In monitoring of, for example, a chemical process a length of below 10 meters, for example 1 meter may be suitable.

It should be noted that in the above described embodiments light that is back reflected from a binding portion is detected. The person skilled in the art realises that according to other embodiments light reflected and or scatter by the binding portion may be detected after it is transmitted in a forward direction, i.e. away from the light source. In other words, light is sent in via a light entrance may propagate within the optical fibre and after interaction with a binding portion be transmitted to a light exit. The light being transmitted from a binding portion to which a compound has been bound may be different compared to light transmitted from that binding portion without a bound compound. Hence a change in light transmitted to the light exit may be used to determine the binding of the compound. To this end the light source and the detector may be arranged at different location along the optical fibre.

Alternatively, the optical fibre may comprise a mirror at an end portion of the optical fibre such that light transmitted from the binding portion may be reflected at the mirror and thereafter transmitted to the detector.

Figure 6:
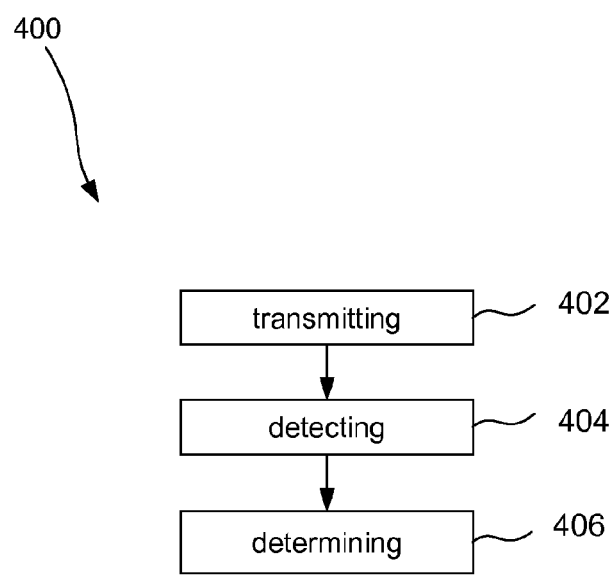
FIG. 6 illustrates a method for analysis of a fluid at a plurality of locations.

FIG. 6 illustrates a method for analysis of a fluid at a plurality of locations using the system, wherein at least a portion of the optical fibre is placed in the fluid such that the at least two binding portions are arranged at different locations within the fluid wherein the at least two binding portions are arranged for binding the same compound or compounds. The method 400 comprising transmitting 402 light through the optical fibre and thereby to each of the at least two binding portions, detecting 404 light transmitted through the at least two binding portions, or light reflected back from the at least two binding portions, determining 406 if one or more compounds are bound to the least two binding portions respectively.

The method 400 may further comprise comparing data resulting from the determining pertaining to one of the at least two binding portions, with data resulting from the determining pertaining to another one of the at least two binding portions. The above mentioned features of the optical fibre and the system, when applicable, apply to the method as well. In order to avoid undue repetition, reference is made to the above. The person skilled in the art further realizes that the present invention by no means is limited to the preferred embodiments described above. On the contrary, many modifications and variations are possible within the scope of the appended claims.

For example, the system 200 further comprises a transceiver, for transceiving data to, from, or within the system 200. The transceiver may use electromagnetic fields to send or receive data from the system 200 within a communication network.

The system 200 may further comprise a data processor and a memory. The data processor may for example be arranged to process data obtained by the detector 208. The obtained data may be stored in the memory. The obtained data may further, for example, be compared to reference data stored in the memory. Alternatively, data resulting from detector 208 and/or data pertaining to analysis of detected light from the optical fibre may be compared to externally stored reference data within a communication network which is accessible to the system via the transceiver. Obtained data from the system 200 may further be sent from the system to an external device such as a computer via the communication network. An external data processor may be arranged outside the system but located within the communication network may further be used to process data obtained by the detector 208. The external data processor may for example be arranged in an external computer. The requirements of the system 200 to process data are thereby reduced. The communication network may be a local area network, a LAN, an internet, or a telecommunication network. Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage.

The invention claimed is:

1. A system for detection of one or more compounds in a fluid, the system comprising:
   an optical fibre comprising:
      a light entrance, and
      at least two binding portions separated from each other along a longitudinal direction of the optical fibre, wherein
      each of the at least two binding portions comprises:
         a plasmonic structure and/or a SERS structure, and
         a binding material for binding one or more compounds,
      at least two of the binding portions are arranged for binding a same compound or compounds,
      the binding material is arranged on the plasmonic structure and/or the SERS structure,
      the optical fibre is arranged for receiving light and transmitting light to each of the at least two binding portions, and
      each of the at least two binding portions is arranged such that
         light transmitted through that binding portion without bound compound is different compared to light transmitted through that binding portion with bound compound, or
         light reflected back from that binding portion without bound compound is different compared to light reflected back from that binding portion with bound compound;
   a light source arranged for transmitting light through the light entrance into the optical fibre and thereby to each of the at least two binding portions, the light source being a pulsed light source; and
   an optical time-domain reflectometer (OTDR) that includes a time resolving detector, wherein the time resolving detector is configured to detect light reflected from each binding portion of the at least two binding portions separately.

2. The system according to claim 1, wherein the light source is a broad band light source.

3. The system according to claim 1, wherein the OTDR further comprises a wavelength dispersing element.

4. The system according to claim 1, further comprising a transceiver for transceiving data to, from, or within the system.

5. The system according to claim 1, wherein
   the optical fibre comprises at least three binding portions, and
   the at least two binding portions are arranged for binding different compounds.

6. The system according to claim 1, wherein the binding material comprises functionalising groups or molecular imprints.

7. A method for analyzing a fluid at a plurality of locations using a system that includes:
   an optical fibre including at least two binding portions separated from each other along a longitudinal direction of the optical fibre, wherein
      each of the at least two binding portions comprises a plasmonic structure and/or a SERS structure, and a binding material for binding one or more compounds,
      at least two of the binding portions are arranged for binding a same compound or compounds,
      the binding material is arranged on the plasmonic structure and/or the SERS structure,
      the optical fibre is arranged for receiving light and transmitting light to each of the at least two binding portions,
      each of the at least two binding portions is arranged such that light transmitted through that binding portion without bound compound is different compared to light transmitted through that binding portion with bound compound, or light reflected back from that binding portion without bound compound is different compared to light reflected back from that binding portion with bound compound, and
      the at least two binding portions are arranged for binding the same compound or compounds,
   a light source arranged for transmitting light through a light entrance of the optical fibre, the light source being a pulsed light source, and
   an optical time-domain reflectometer (OTDR) that includes a time resolving detector,
   the method comprising:
      transmitting, with the light source, light through the optical fibre and to each of the at least two binding portions;
      detecting, with the OTDR, light reflected from each binding portion of the at least two binding portions separately; and
      determining, based on the detecting, if one or more compounds are bound to the least two binding portions respectively.

8. The method according to claim 7, further comprising:
   comparing first data with second data, the first resulting from the determining pertaining to one of the at least two binding portions and the second data resulting from the determining pertaining to another one of the at least two binding portions.

\* \* \* \* \*